(12) United States Patent
Zhang

(10) Patent No.: US 12,338,251 B2
(45) Date of Patent: Jun. 24, 2025

(54) SUBSTITUTED MACROCYCLES USEFUL AS KINASE INHIBITORS

(71) Applicant: TELIGENE LTD, Suzhoou (CN)

(72) Inventor: Dawei Zhang, Thousand Oaks, CA (US)

(73) Assignee: TELIGENE US LLC, Thousand Oaks, CA (US)

( * ) Notice: Subject to any disclaimer, the term of this patent is extended or adjusted under 35 U.S.C. 154(b) by 716 days.

(21) Appl. No.: 17/577,291

(22) Filed: Jan. 17, 2022

(65) Prior Publication Data

US 2022/0135592 A1 May 5, 2022

Related U.S. Application Data

(63) Continuation of application No. PCT/CN2020/090070, filed on May 13, 2020.

(60) Provisional application No. 62/920,732, filed on May 14, 2019.

(51) Int. Cl.
*C07D 498/18* (2006.01)
*A61P 35/00* (2006.01)

(52) U.S. Cl.
CPC ............ *C07D 498/18* (2013.01); *A61P 35/00* (2018.01)

(58) Field of Classification Search
CPC ................................ C07D 498/18; A61P 35/00
See application file for complete search history.

(56) References Cited

U.S. PATENT DOCUMENTS 10,159,663 B2   12/2018 Xia et al.
2017/0216264 A1  8/2017 Xia et al.

FOREIGN PATENT DOCUMENTS

CN     103373986 A     10/2013
WO     2016026423 A1    2/2016
WO     WO8016026423 A1 *  2/2016 ........... C07D 498/18

OTHER PUBLICATIONS

International Search Report issued on Aug. 12, 2020 for PCT/CN2020/090070.

* cited by examiner

*Primary Examiner* — Dale R Miller
*Assistant Examiner* — Samantha Lynn Schachermeyer

(57) ABSTRACT

Disclosed herein are novel substituted macrocycle compounds according to Formula I, or pharmaceutically acceptable salts, solvates, or enantiomers thereof. The compounds and compositions of the present invention have protein kinases inhibitory activities and are expected to be useful for the treatment of protein kinases mediated diseases and conditions.

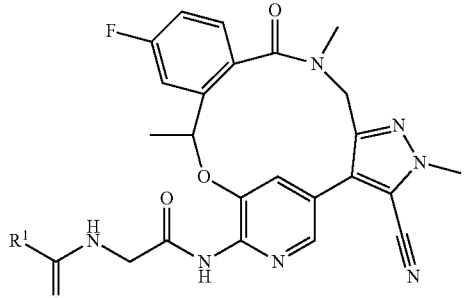

$R^1$ is $C_{1-6}$ alkyl, or $C_{1-6}$ alkoxy

20 Claims, No Drawings

SUBSTITUTED MACROCYCLES USEFUL AS KINASE INHIBITORS

CROSS-REFERENCE

This application is a continuation of Application No. PCT/CN2020/090070, filed on May 13, 2020, which claims the benefit of U.S. Provisional Application No. 62/920,732, filed on May 14, 2019, each of which is incorporated herein by reference in its entirety.

FIELD OF THE DISCLOSURE

Disclosed herein are inhibitors of kinase and pharmaceutically acceptable salts, solvates, hydrates, prodrugs and metabolites thereof, the preparation method thereof, and the use of such compounds to treat kinase mediated diseases and conditions such as cancer.

BACKGROUND OF THE DISCLOSURE

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. Examples of kinases in the protein kinase family include, without limitation, Abl1 (v-Abl Abelson murine leukemia viral oncogene homolog 1), Akt, Alk, Bcr-Abl1, Blk, Brk, Btk, c-Kit, c-Met, c-Src, c-Fms, CDK1-10, b-Raf, c-Raf1, CSF1R, CSK, EGFR, ErbB2, ErbB3, ErbB4, Erk, FGFR1, FGFR2, FGFR3, FGFR4, FGFR5, Flt-1, Fps, Frk, Jak, KDR, MEK, PDGFR, PIK, PKC, PYK2, Ros, Tie, Tie2, and Zap70. Due to their activity in numerous cellular processes, protein kinases have emerged as important therapeutic targets.

ALK (Anaplastic Lymphoma Kinase) is a 1620 amino acid transmembrane protein, consisting of extracellular domain with amino-terminal signal peptide, intracellular domain with a juxtamembranous segment harboring a binding site for insulin receptor substrate-1, and a carboxy-terminal kinase domain. ALK is a member of the insulin receptor tyrosine kinases, Echinoderm microtubule-associated protein-like 4 (EML4) is a 120 KDa cytoplasmic protein, which involves in the formation of microtubules and microtubule binding protein. EML4-ALK is a novel fusion gene arising from an inversion on the short arm of chromosome 2 that joined exons 1-13 of EML4 to exons 20-29 of ALK. The presence of EML4-ALK fusion is identified in approximately 3-13% of NSCLC (non-small cell lung cancer) patients. To this end, attempts have been made to identify small molecules which act as PK inhibitors. For example, Amino heteroaryl compounds (WO2004/076412) have been described as ALK/c-MET inhibitors. Aza-indole derivatives (WO2010/068292) have been described as ALK/EGFR kinase inhibitors.

Thus, the compounds that can inhibit protein kinases such as ALK and other kinases activity either independently or together can be used to treat human diseases such as cancers.

However, there is still a huge unmet medical need for overcoming the resistance of ALK mutation as well as improving the safety profile of ALK inhibitor.

INCORPORATION BY REFERENCE

The contents of all references, patents, pending patent applications and published patents, cited throughout this application are hereby expressly incorporated by reference.

SUMMARY OF THE DISCLOSURE

In one aspect, there are provided compounds of Formula I:

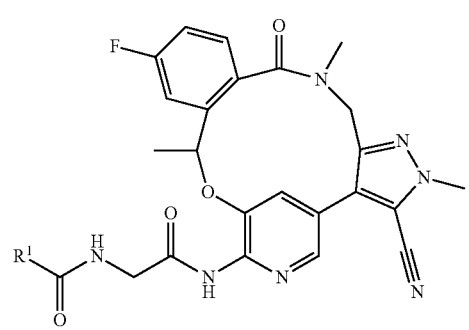

or a pharmaceutically acceptable salt, solvate or enantiomer, or prodrug or metabolite thereof,
wherein
$R^1$ is $C_{1-6}$ alkyl, or $C_{1-6}$ alkoxy.

In another aspect, the present application further provides pharmaceutical compositions comprising a compound of Formula I described above and a pharmaceutically acceptable carrier.

In another aspect, the present application further provides methods for treating or preventing a kinase mediated disorder comprising administrating to a mammalian subject a therapeutically effective amount of any of the compounds of Formula I described above.

DETAILED DESCRIPTION OF THE DISCLOSURE

In some embodiments of the present disclosure, there are provided compounds of Formula I:

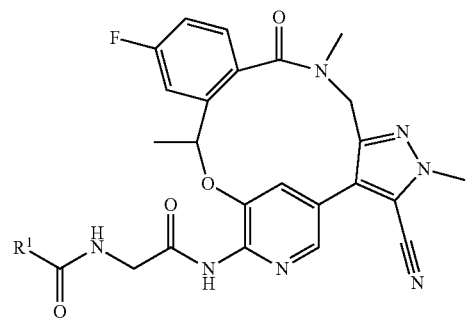

or a pharmaceutically acceptable salt, solvate or enantiomer, or prodrug or metabolite thereof,
wherein
$R^1$ is $C_{1-6}$ alkyl, or $C_{1-6}$ alkoxy.

In some embodiments of the present disclosure, there are provided compounds of Formula II:

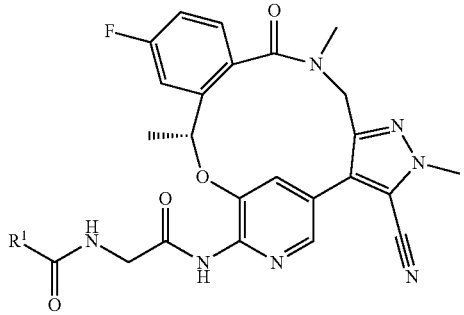

II or a pharmaceutically acceptable salt, solvate or enantiomer, or prodrug or metabolite thereof, wherein $R^1$ is $C_{1-6}$ alkyl, or $C_{1-6}$ alkoxy.

In some embodiments of the present disclosure, $R^1$ is methyl, ethyl, n-propyl, isopropyl, n-butyl, sec-butyl, iso-butyl, or tert-butyl.

In one embodiments of the present disclosure, $R^1$ is methyl.

In some embodiments of the present disclosure, $R^1$ is methoxyl, ethoxyl, n-propoxyl, isopropoxyl, n-butoxyl, sec-butoxyl, iso-butoxyl, or tert-butoxyl.

In one embodiments of the present disclosure, $R^1$ is methoxyl.

In one embodiments of the present disclosure, $R^1$ is ethoxyl.

In certain embodiments, there are provided compounds without limitation selected from the group consisting of:

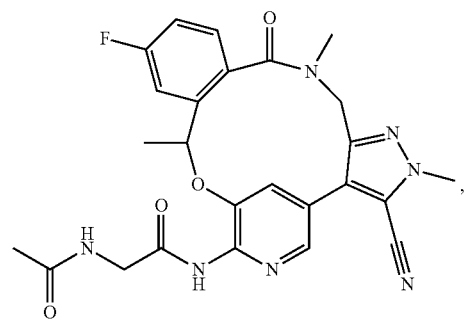

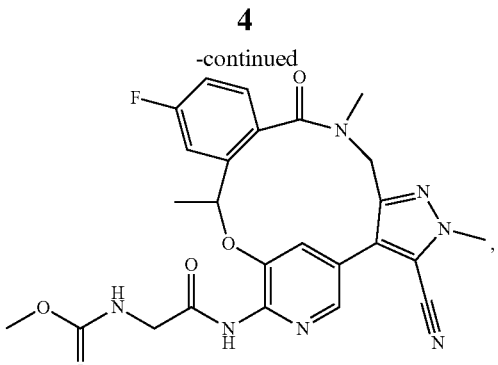

and the like, or a pharmaceutically acceptable salt, solvate, or a prodrug, or a metabolite thereof.

In certain embodiments, there are provided compounds without limitation selected from the group consisting of:

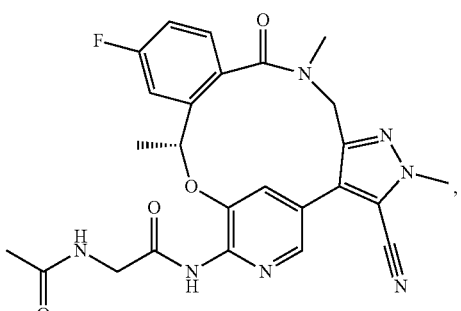

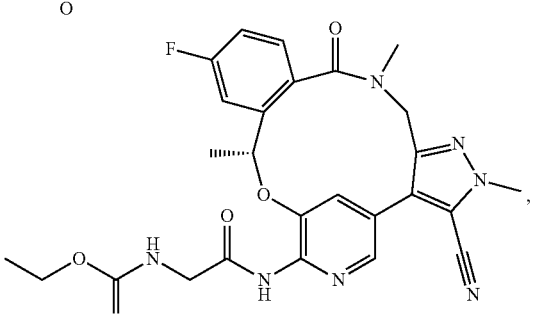

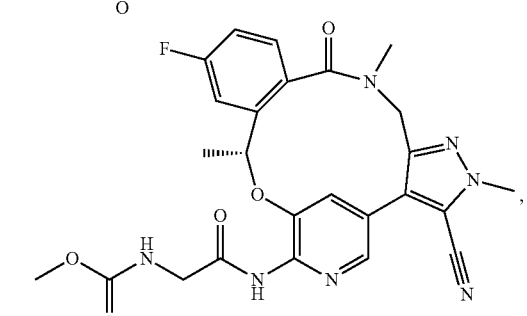

and the like, or a pharmaceutically acceptable salt, solvate, or prodrug, or metabolite thereof.

In other embodiments, the compound of this disclosure is in the form of pharmaceutically acceptable salt. In some embodiments, the compound of this disclosure is in the form of a solvate. In other embodiments, the compound of this disclosure is in the form of a metabolite. In other embodiments, the compound of this disclosure is in the form of a prodrug. In some embodiments, the compound of this disclosure is an enantiomer. In other embodiments, the compound of this disclosure is a diastereomer. In another embodiment, the deuterium enrichment in compounds of this disclosure is at least about 1%.

In some embodiments, there are provided pharmaceutical compositions comprising a compound of the disclosure and a pharmaceutically acceptable carrier. In certain embodiments, the compositions are for the treatment of a disease regulated by a protein kinase. In certain embodiments, the compositions are for the prevention or the treatment of a hyper-proliferative disorder and/or angiogenesis disorder. In some embodiments, the pharmaceutical compositions further comprise an anti-neoplastic agent, an immunosuppressant, an immunostimulant, or combination thereof. In other embodiments, the pharmaceutical compositions are suitable for oral, parenteral, or intravenous administration.

In some embodiments, the present disclosure provides methods for regulating the kinase signaling transduction comprising administrating to a mammalian subject a therapeutically effective amount of any of the inventive compounds described herein.

In other embodiments provide herein methods for treating or preventing a ALK (including all fusion and/or mutant kinases), ROS1, and/or NTRK kinases mediated disorder, said method comprises administrating to a mammalian subject a therapeutically effective amount of any of the inventive compounds described herein.

In other embodiments, there are provided herein methods for treating neoplasia comprising administrating to a mammalian subject in need thereof, a therapeutically effective amount of any of the inventive compounds described herein. In certain embodiments, the neoplasia is selected from skin cancer, leukemia, colon carcinoma, renal cell carcinoma, gastrointestinal stromal cancer, solid tumor cancer, myeloma, breast cancer, pancreatic carcinoma, non-small cell lung cancer, non-Hodgkin's lymphoma, hepatocellular carcinoma, thyroid cancer, bladder cancer, colorectal cancer, prostate cancer, and brain cancer. In some embodiments, the methods further comprise administering one or more anti-cancer agents.

The following definitions can assist in understanding the disclosure described herein.

The term "alkyl" is intended to include straight, branched, and cyclic hydrocarbon groups, which contain only single carbon-carbon bonds and which may be unsubstituted or optionally substituted with one or more functional groups. The preferred chain length of an alkyl group is from 1 to 6 carbon atoms. $C_1$-$C_6$ alkyl is intended to include $C_1$ (methyl), $C_2$ (ethyl), $C_3$ (n-propyl, isopropyl), $C_4$ (e.g. n-butyl, isobutyl, sec-butyl, tert-butyl), $C_5$ (e.g. n-pentyl) and $C_6$ alkyl groups. Alkyl may be substituted or unsubstituted. Illustrative substituted alkyl group include, but are not limited to, fluoromethyl, difluoromethyl, trifluoromethyl, aminomethyl, aminoethyl, hydoxymethyl, methoxymethyl, 2-fluoroethyl, and 2-methoxyethyl, etc.

The term "alkoxy" refers to either an —O-(alkyl) or an —O-(unsubstituted cycloalkyl) group. $C_1$-$C_6$ alkoxy is intended to include $C_1$-$C_6$ alkyl groups, wherein $C_1$-$C_6$ alkyl is defined above. Representative examples include, but are not limited to, methoxy, ethoxy, propoxy, butoxy, cyclopropyloxy, cyclobutyloxy, cyclopentyloxy, cyclohexyloxy, and the like.

The term "pharmaceutically acceptable" when used with reference to a compound of this disclosure is intended to refer to a form of the compound that is safe for administration to a subject. For example, a free base, a salt form, a solvate, a hydrate, a prodrug or derivative form of a compound of this disclosure, which has been approved for mammalian use, via oral ingestion or any other route of administration, by a governing authority or regulatory agency, such as the Food and Drug Administration (FDA) of the United States, is pharmaceutically acceptable.

The phrase "effective amount" is intended to quantify the amount of each agent, which can achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Starting materials of the disclosure, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

In synthesizing a compound of formula I according to a desired procedure, the steps in some embodiment, are performed in an order suitable to prepare the compound, including a procedure described herein or by an alternate order of steps described herein, and in one embodiment, be preceded, or followed, by additional protection/deprotection steps as necessary. The intermediates in some embodiments are isolated or carried on in situ, with or without purification. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

The compounds of this disclosure in some embodiments also are represented in multiple tautomeric forms. The disclosure expressly includes all tautomeric forms of the compounds described herein.

The compounds in one embodiment also occur in cis- or trans- or E- or Z-double bond isomeric forms. All such isomeric forms of such compounds are expressly included in the present disclosure.

Indications

The present disclosure provides compounds which are capable of modulating one or more signal transduction pathways comprising, but not limited to ALK.

By the term "modulating," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

The compounds of the present disclosure can also modulate one or more of the following processes, including, but not limited to, e.g., cell growth (including, e.g., differentiation, cell survival, and/or proliferation), tumor cell growth (including, e.g., differentiation, cell survival, and/or proliferation), tumor regression, endothelial cell growth (including, e.g., differentiation, cell survival, and/or proliferation), angiogenesis (blood vessel growth), lymph angiogenesis (lymphatic vessel growth), and/or hematopoiesis (e.g., T- and B-cell development, dendritic cell development, etc.).

While not wishing to be bound by any theory or mechanism of action, it has been found that compounds of the present disclosure possess the ability to modulate kinase activity. The methods of the present disclosure, however, are not limited to any particular mechanism or how the compounds achieve their therapeutic effect. By the phrase "kinase activity," it is meant a catalytic activity in which a gamma-phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), by binding to and locking the kinase in an inactive conformation, etc.

Formulations and Method of Use

The amount of compound(s) which is/are administered and the dosage regimen for treating cancer with the compounds and/or compositions of this disclosure depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg may be appropriate, and can be useful for all methods of use disclosed herein. The daily dose can be administered in one to four doses per day.

While it may be possible to administer a compound of the disclosure alone, in the methods described, the compound administered normally can be present as an active ingredient in a pharmaceutical composition. Thus, in another embodiment of the disclosure, there is provided a pharmaceutical composition comprising a compound of this disclosure in combination with a pharmaceutically acceptable carrier, which includes diluents, excipients, adjuvants and the like (collectively referred to herein as "carrier" materials) as described herein, and, if desired, other active ingredients. A pharmaceutical composition of the disclosure may comprise an effective amount of a compound of the disclosure or an effective dosage amount of a compound of the disclosure. An effective dosage amount of a compound of the disclosure includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

The compounds of the disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

The compounds of the disclosure may also be used in fast-dissolving, fast-disintegrating dosage forms such as those described in Expert Opinion in Therapeutic Patents, 11(6), 981-986 by Liang and Chen (2001), the disclosure of which is incorporated herein by reference in its entirety.

Formulations for parenteral administration may be formulated to be immediate and/or modified release. Modified release formulations include delayed-, sustained-, pulsed-, controlled-, targeted and programmed release. Thus compounds of the disclosure may be formulated as a solid, semi-solid, or thixotropic liquid for administration as an implanted depot providing modified release of the active compound. Examples of such formulations include drug-coated stents and PGLA microspheres.

Combinations

While the compounds of the disclosure can be dosed or administered as the sole active pharmaceutical agent, they can also be used in combination with one or more compounds of the disclosure or in conjunction with other agents. When administered as a combination, the therapeutic agents can be formulated as separate compositions that are administered simultaneously or sequentially at different times, or the therapeutic agents can be given as a single composition.

The synthesis of compounds in the disclosure was described in the following Scheme 1.

The synthesis of compounds of Formula I was described in Scheme 1. The starting material Compound 1 was prepared following similar literature known procedures. The amide formation reaction of Compound 1 and substituted Glycine afforded compounds of Formula I.

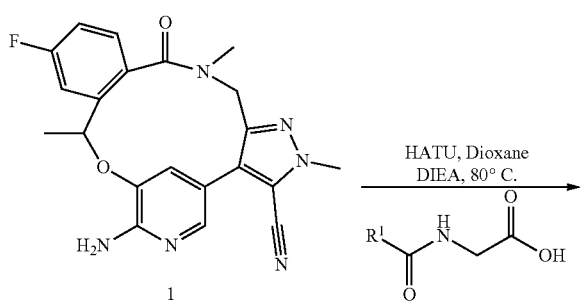

Scheme 1

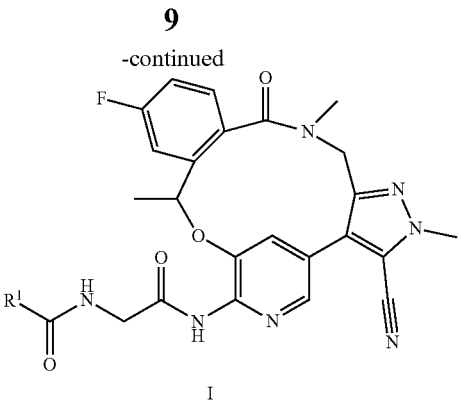

I

The synthesis of compounds of Formula II was described in Scheme 2. The starting material Compound 2 was prepared following the known literature procedure. The acylation reaction of Compound 2 afforded compounds of Formula II.

Scheme 2

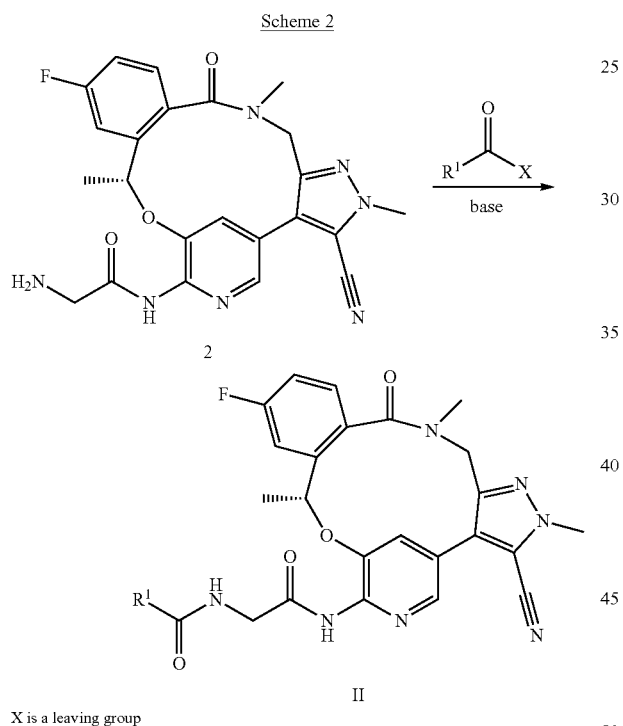

X is a leaving group

Proton NMR Spectra

Unless otherwise indicated, all ¹H NMR spectra were run on a Varian series Mercury 300, 400, 500 MHz instrument or a Bruker series 400, 500 MHz instrument. Where so characterized, all observed protons are reported as parts-per-million (ppm) downfield from tetramethylsilane (TMS) or other internal reference in the appropriate solvent indicated.

Abbreviations

DCM means dichloromethane.
EA means ethyl acetate.
TLC means thin layer chromatography.
HATU means 1-[bis(dimethylamino)methylene]-1H-1,2,3-triazolo[4,5-b]pyridinium 3-oxid hexafluorophosphate.
DIPEA means diisopropylethylamine.
HPLC means high-performance liquid chromatography.
LC-MS means liquid chromatography-mass spectrometry.
NMR means nuclear magnetic resonance.

Example 1: The Synthesis of Compound 3

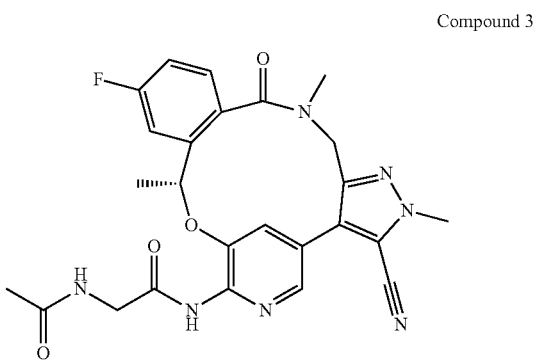 [SMILES: CC(=O)NCC(=O)Nc1ncc2cc1O[C@H](C)c1cc(F)ccc1C(=O)N(C)Cc1nn(C)c(C#N)c1-2]

Compound 3

To a solution of Compound 2 (1 g) in DCM (15 mL) was added pyridine (263.1 mg, 1.5 eq) at 0° C. and stirred for 0.5 h. Then acetyl chloride (208.9 mg, 1.2 eq) was added to the reaction mixture in several times. The reaction was stirred 0.5 hours at 0° C., and TLC indicated completion of the reaction. Then water (20 mL) was added to the reaction. The layers were separated and the aqueous layer was extracted with DCM (2×10 mL). The combined organic layers were washed with brine (20 mL), dried over anhydrous sodium sulfate. The crude product was purified by preparative TLC plate to give Compound 3 as a solid (782.3 mg). ¹H-NMR (400 MHz, CDCl$_3$): 1.867-1.852 (d, J=6, 3H), 2.139 (s, 3H), 3.160 (s, 3H), 4.130 (s, 3H), 4.396-4.489 (q, J$_1$=14.4, J$_2$=8.4, 2H), 4.613 (s, 2H), 5.796-5.816 (q, J$_1$=4.8, J$_2$=1.6, 1H), 6.499-6.522 (t, J$_1$=4.8, J$_2$=4.4, 1H), 7.230-7.285 (m 1H), 7.375-7.379 (d, J=1.6, 1H), 8.139 (s, 1H), 8.143 (s, 1H); LC-MS (M+1=506).

Example 2: The Synthesis of Compound 4

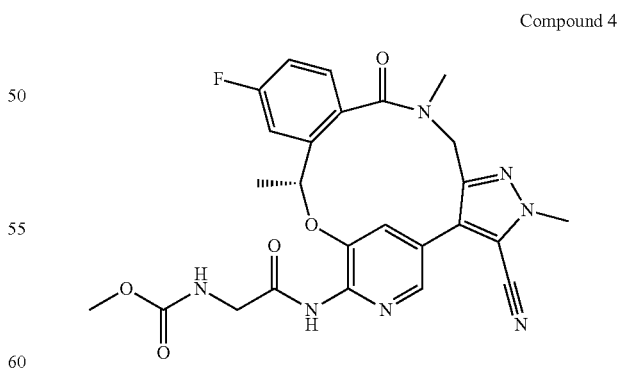

Compound 4

To a solution of Compound 1 (200 mg) in toluene (20 mL) was added (methoxycarbonyl)glycine (78.6 mg, 1.2 eq), HATU (280.8 mg, 1.5 eq) and DIPEA (127 mg, 2 eq) at room temperature and stirred. The reaction was stirred for 5 hours at reflux and removed the water with a water separator. TLC indicated completion of the reaction, then water (30 mL)

was added to the reaction, the aqueous layer was extracted with ethyl acetate (EA) (3×10 mL). The combined organic layers were washed with brine (20 mL), dried over anhydrous sodium sulfate. The crude product was purified by preparative TLC to give Compound 4 as a solid (146.6 mg). $^1$H-NMR (400 MHz, CDCl$_3$): 1.840-1.856 (d, J=6.4, 3H), 3.158 (s, 3H), 3.782 (s, 3H), 4.130 (s, 3H), 4.434-4.491 (m, 4H), 5.655 (s, 1H), 5.790-5.810 (q, J$_1$=4.8, J$_2$=1.6, 1H), 7.025-7.092 (m, 2H), 7.232-7.267 (m 1H), 7.334-7.355 (d, J=8.4, 1H), 8.138-8.142 (s, 1H), 8.607 (s, 1H). LC-MS (M+1=522).

Example 3: The Synthesis of Compound 5

Compound 5

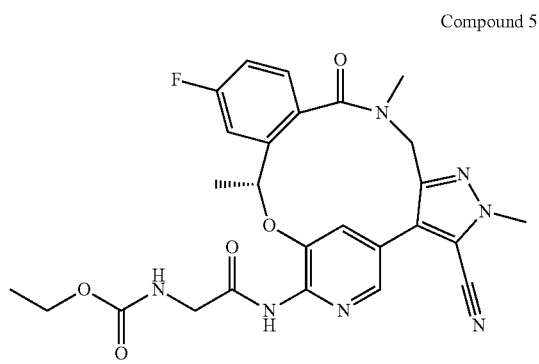 [SMILES: CCOC(=O)NCC(=O)Nc1ncc2cc1O[C@H](C)c1cc(F)ccc1C(=O)N(C)Cc1nn(C)c(C#N)c1-2]

To a solution of Compound 1 (100 mg) in DCM (5 mL) was added (ethoxycarbonyl)glycine (54.3 mg, 1.5 eq), HATU (187.2 mg, 2 eq) and DIPEA (80 mg, 2.5 eq) at room temperature and stirred. The reaction was stirred for 8 hours at reflux, then water (5 mL) was added to the reaction. The aqueous layer was extracted with DCM (3×5 mL). The combined organic layers were washed with brine (10 mL), dried over anhydrous sodium sulfate. The crude product was purified by preparative TLC to give Compound 5 as a solid (40.8 mg). $^1$H-NMR (400 MHz, CDCl$_3$): 1.263-1.354 (m, 3H), 1.839-1.855 (d, J=6.4, 3H), 3.159 (s, 3H), 4.117-4.131 (s, 3H), 4.199-4.252 (q, J$_1$=7.2, J$_2$=6.8, 2H), 4.399-4.522 (m, 4H), 5.58 (s, 1H), 5.795-5.811 (q, J$_1$=4.8, J$_2$=1.6 1H), 7.047-7.090 (m 2H), 7.232-7.267 (m, 1H), 7.324-7.344 (d, J=8, 1H), 8.142 (s, 1H), 8.146 (s, 1H). LC-MS (M+1=536).

Biological Assays:

As stated hereinbefore, the compounds disclosed in the present disclosure possess anti-proliferation activity. These properties may be assessed, for example, using one or more of the procedures set out below:

An in vitro assay which determines the ability of a test compound to inhibit kinase.

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for quantitative polymerase chain reaction (qPCR) detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% bovine serum albumin (BSA), 0.05% Tween 20, 1 mM dithiothreitol (DTT)) to remove unbound ligand and to reduce non-specific binding. Binding reactions were assembled by combining kinases, liganded affinity beads, and test compounds in 1× binding buffer (20% SeaBlock, 0.17× phosphate buffered saline (PBS), 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM non-biotinylated affinity ligand) and incubated at room temperature with shaking for 30 minutes. The kinase concentration in the eluates was measured by qPCR.

A Representative Number of Compounds were Assayed Against BAF$_3$ Cell Lines Using the Cell Proliferation Assays:

Cell Culture and Inoculation:

1. Cells in logarithmic growth phase were harvested and counted by platelet counter. Trypan blue exclusion method was used to detect the cell viability to ensure that the cell viability was above 90%.

2. Adjust the cell concentration; 90 µL cell suspension was added to 96 well plates respectively.

3. Cells in 96-well plate were cultured overnight at 37° C., 5% CO$_2$ and 95% of humidity.

Drug Dilution and Dosing:

1. Prepare 10-fold drug solution with the highest concentration of 100 µM, 9 concentrations and 3.16-fold dilution. Add 10 µL of drug solution to each well of 96-well plate inoculated with cells, and set up 3 duplicate wells for each drug concentration.

2. Cells in 96-well plates with drug added were cultured for 72 hours at 37° C., 5% CO$_2$ and 95% of humidity, and then CELLTITER-GLO® (CTG) analysis was performed.

End Reading Board:

1. Melt CTG reagent and equilibrate cell plates to room temperature for 30 minutes.

2. Add an equal volume of CTG solution to each well.

3. Vibrate on a fixed-orbit shaker for 5 minutes to lyse cells.

4. Place the cell plate at room temperature for 20 minutes to stabilize the cold light signal.

5. Read the cold light value.

The data were analyzed by GraphPad Prism 5.0 software, and the dose-effect curve was obtained by fitting the data by nonlinear S-curve regression, and IC$_{50}$ value was calculated accordingly.

Cell survival rate (%)=(Lum$_{drug\ to\ be\ tested}$−Lum$_{culture\ solution\ control}$)/(Lum$_{cell\ control}$−Lum$_{culture\ solution\ control}$)×100%. Lum is luminescence.

The following Table A lists compounds representative of the disclosure and their activity in cell assays.

TABLE A

| | Cell proliferation Assays | |
|---|---|---|
| Compound | Ba/F3 EML4-ALK-WT (IC$_{50}$) | Ba/F3 EML4-ALK-L1196M (IC$_{50}$) |
| 3 | 0.0028 µM | 0.051 µM |

A Representative Number of Compounds were Tested in P450 3A4 Assay in Human Liver Microsomes to Measure CYP Inhibition:

Human liver microsomes (HLM) are stored at −80° C. Before the study, microsomes were thawed in a cold water bath, and then were put on ice immediately. Test compounds and P450 3A4 specific inhibitor ketoconazole were dissolved in DMSO to yield a stock solution of 10 mM. The stock solution was diluted with 50% acetonitrile to get a working solution at the concentration of 1.5 mM. The working solution was further diluted with 0.1 M potassium phosphate buffer to get a series of working solution at concentrations of 150, 50, 15, 5, 1.5, 0.5, 0.15, and 0.05 µM. Incubation mixtures in duplicate contain pooled human liver microsome (0.1 mg/mL), 3.3 mM $MgCl_2$, CYP 3A4 probe substrate testosterone (50 µM), specific inhibitor or test compounds (30, 10, 3, 0.1, 0.03, 0.01, 0.003, 0.01 µM) in 0.1 M potassium phosphate buffer (total volume 0.1 mL). Negative control contains 0.1 M phosphate buffer instead of a specific inhibitor or test compound. The final concentrations of DMSO and acetonitrile were equal to or less than 0.1%. The mixtures are pre-incubated for 10 min at 37° C. Then, 1 mM NADPH is added to initiate a reaction. Following a 10-min incubation at 37° C., the reactions are terminated by the addition of 300 µL acetonitrile containing an internal standard. The formation of the corresponding products is detected by LC/MS/MS.

LCMS method: A Waters ACQUITY UPLC system coupled API 4000 Qtrap system was used. The mass spectrometer is equipped with Turbo Ion Spray (ESI) Interface (Applied Biosystems, Concord, Ontario, Canada). Analyst 1.5 software packages (Applied Biosystems) were used to control the LC-MS/MS system, as well as for data acquisition and processing. Chromatographic separation was achieved on Waters ACQUITY UPLC BEH C18 column (50×2.1 mm ID, 1.7 µm). The column temperature was maintained at ambient temperature (25° C.). The mobile phase A is pure water supplemented with 0.1% formic acid (v/v). The mobile phase B is acetonitrile supplemented with 0.1% formic acid (v/v). The flow rate was maintained at 0.6 mL/min.

Sample Preparation: The reactions were quenched by the addition of a 3-fold volume of ice-cold methanol/acetonitrile (1/1, v/v) mix containing an internal standard. The mixture was centrifuged at 4000 rpm for 20 min. 100 µL of supernatant was mixed with 200 µL of $H_2O$ and the final solution was injected for LC-MS/MS analysis.

Data Analysis: The peak area ratio of the product (6β-hydroxytestosterone) to internal standard is plotted as a percentage of the relevant negative control for each reaction to represent the residual enzymatic activity. The $IC_{50}$ value of a test compound is determined by nonlinear regression of a plot enzymatic activity versus inhibitor concentration using GraphPad Prism software. The general criteria to evaluate the potential risk of drug-drug interaction (DDI) is as followed:

$IC_{50}$>10 µM CYP inhibition low;
3 µM<$IC_{50}$<10 µM CYP inhibition moderate
$IC_{50}$<3 µM CYP inhibition high The following Table B lists compounds representative of the disclosure and their activity in Cytochrome P450 3A4 Assay. Compound 3 showed much weaker inhibition for CYP 3A4, indicating much less likely for drug-drug interactions.

TABLE B

| CYP 3A4 inhibition | |
|---|---|
| Compound | CYP 3A4 ($IC_{50}$) |
| Lorlatinib | 7.8 µM |
| 2 | 10 µM |
| 3 | 279 µM |

Solubility Measurement:

Preparation of reference standard solution: 2 mg of Compound was added individually to 100 mL volumetric flask each. The compound was diluted with acetonitrile to 100 mL.

Preparation of sample solution: 2 mg of Compound was added individually to 2 mL eppendorf tube (EP), followed by addition of 1 mL of pH 7.0 or 10.0 buffer solution (20 mM). The solution was shaken for 2 minutes and left for 30 minutes at 25° C. After standing for 30 minutes, precipitate was formed in the bottom of the EP. The solutions were filtered through a 0.2 um membrane filter, and then diluted by 50 times with water.

The standard and sample solutions were injected into the HPLC on a Shim-Pack CLC-ODS C18 column (150 mm×6.0 mm, 5 µm) with the same volume. The mobile phase consisted of acetonitrile with 2% trichloromethane—20 mM $KH_2PO_4$ buffer (pH=7.0) at a flow rate of 1 mL/minute (40:60). The detection wavelength is at 264 nm. Calculation: solubility of sample=the concentration of standard× Area of sample×50/Area of standard. Compound 3 had much higher solubility than compound 2 and Lorlatinib at pH=7.0.

TABLE C

| Solubility of Compounds of the disclosure | | | |
|---|---|---|---|
| | Lorlatinib (PF-06463922) | Compound 2 | Compound 3 |
| Solubility at pH 7.0 | 0.029 mg/mL | 0.091 mg/mL | 0.772 mg/mL |

In Vivo Xenograft Assay:

A representative protocol for the in vivo experiment is as followed to establish the subcutaneous $BaF_3$—SLC34A2-ROS1 cell line xenograft model in nude mice and to evaluate the in vivo therapeutic efficacy of the compounds:

Animals: Male Balb/c nude mice (6~8 weeks old) were obtained from SLAC Laboratory Animal, Shanghai, China. Animals were maintained under SPF conditions in sterile filter top cages and housed on HEPA-filtered ventilated racks. Animals received sterile rodent chow and water ad libitum.

Cell line: $BaF_3$—SLC34A2-ROS1, S.C.

Xenograft Models in Athymic Mice: Cells for implantation into athymic mice were harvested and pelleted by centrifugation at 1200 r/min for 5 min. Cells were washed once and resuspended in sterile PBS buffer with $5×10^6$ in 200 µl. Then cells were implanted s.c. into the right scapular region of each mouse and allowed to grow to 200-300 $mm^3$ before the administration of compound.

Preparation of the Dose Formulation: each compound was suspended in 0.5% sodium carboxymethyl cellulose (CMC-Na).

Randomization: When tumor volumes approach 200-300 $mm^3$, the mice are randomized into 5 groups according to the tumor volume. The day is denoted as D1 and the treatments starts at this day.

Administered: Dose is administered with an oral gavage needle once daily for a number of days. Treatment of compounds administered in 0.5% CMC-Na by p.o. gavage was initiated when tumors were 200-300 $mm^3$ in volume.

Observations: After inoculation, the animals are checked daily for morbidity and mortality. At the time of routine monitoring, the animals are checked for any effects of tumor growth and treatments on normal behavior such as mobility, body weight gain/loss (body weights are measured twice weekly or every other day), eye/hair matting and any other abnormal effect. Death and observed clinical signs are recorded on the basis of the numbers of animals within each subset.

Tumor Size Measurements: Tumor volume was determined by measurement with electronic vernier calipers every 3 days and tumor volume was calculated as the product of its length×width2×0.5.

Effect studies: Tumor volume was expressed on indicated days as the mean tumor volume ±SD.

Percentage (%) inhibition values were measured for drug-treated mice compared with vehicle-treated mice and are calculated as follows: Tumor growth inhibition (TGI, %)=100−[MTV treated/MTV control]×100, where MTV is the median tumor volume. Significant differences between the treated versus the control groups (p<0.05) were determined using t test. At study endpoint, after blood collection, mice were practiced euthanasia by cervical dislocation, the tumor tissue was collected first, then abdominal cavity was cut open, liver and spleen were excised, then weight after the gallbladder was removed respectively. Organ weight and Organ/body weight ratios between the treated versus the control groups were compared.

Ratios was calculated as follows: Ratios=Organ weight/(body weight−tumor weight). Both organ weight and Organ/body weight ratios were also expressed as mean±SD, and significant differences between the treated versus the control groups (p<0.05) were determined using t test.

The following Table D lists compounds representative of the disclosure and their activity in subcutaneous BaF3-SLC34A2-ROS1 cell line xenograft model in nude mice described above. Compound 1 and 3 were dosed at 5 mg/kg by oral gavage once daily for a number of days. Tumor size was weighted. At day 20, Compound 3 showed significant better tumor growth inhibition compared with Lorlatinib. The remaining tumor weight for Compound 3 is much smaller than Lorlatinib (PF-06463922).

TABLE D

| Tumor weight at Day 20 | | | |
|---|---|---|---|
| | Control | Lorlatinib | 3 |
| Tumor weight | 2.118 g | 0.531 g | 0.327 g |

PK Study:

A representative protocol for the PK (pharmacokinetic) assay was as followed: Compounds were given either IV or orally to the same animals. The dose for each compound was 1 mg/kg (volume 5 ml/kg) IV and 10 mg/kg (volume 10 ml/kg) orally. The formulation for IV was in 10% SOLU-TOL® HS 15+90% Phosphate-Buffered Saline at 0.4 mg/mL. A 100% (0.5% Tween 80 in 0.5% methylcellulose (MC) in water) at 0.5 mg/mL suspension was used for the oral formulation. Sample collection: for the IV route, plasma samples were collected at the time points of 0.083, 0.25, 0.5, 1, 2, 4, 8 and 24 hr. For the oral route, plasma samples were collected at the time points of 0.25, 0.5, 1, 2, 4, 8 and 24 hr. Total bioavailability is calculated by adding parent compound and major metabolites. Analysis: LC-MS/MS was used to calculate PK parameters: $t_{1/2}$, $t_{max}$, $C_{max}$, Vss and AUC, etc.

The following Table E lists selected compounds and their bioavailability (F).

| Compound | Total F (%) |
|---|---|
| 2 | 49 |
| 3 | 100 |
| 4 | 100 |

In rats, Compound 2 demonstrated 49% oral bioavailability. Compound 3 and 4 have much improved bioavailability (F=100%).

Toxicity Studies

A number of representative compounds, including Lorlatinib (PF-06463922) and Compound 3, were tested in a typical one-month toxicity studies in rats with dosages 8 mg/kg/day for the females and 16 mg/kg/day for the males. Under the conditions of this experiment, at the end of the compound administration period and the end of the recovery period, #LYMPH and Red blood cell are decreased in blood of some animals in the group administered with Lorlatinib dosages, and Platelet and/or % NEUT shows an increasing trend. The corresponding animal displayed shorten time in Prothrombin time. In contract, similar changes were not observed in the Compound 3 at the same dosages or the vehicle control group.

Stability test: The compounds were tested for their stability at 25° C. for one month, using HPLC to measure the purity. Compound 2 was found decomposed significantly at 25° C., with major impurity A and B increase from 1.13% and 1.39% at Day 0 to 3.98% and 8.34% at Day 30 respectively. Compound 2 is not stable at −30° C. On the other hand, Compounds 3, 4 and 5 showed no significant changes at 0° C. or 25° C. (Table F).

HPLC Method and Condition:

| | |
|---|---|
| Mobile phase A: | 5 mmol/L of solution of potassium dihydrogen phosphate which is adjusted by triethylamine to pH 7.0 |
| Mobile phase B: | acetonitrile |
| Column temperature: | 25° C. |
| Detection wavelength: | 227 nm |
| Injection volume: | 10 μL |
| Flow rate: | 1.0 ml/min |

| Gradient elution | TIME (min) | A % | B % |
|---|---|---|---|
| | 0 | 95 | 5 |
| | 25 | 20 | 80 |
| | 30 | 20 | 80 |
| | 31 | 95 | 95 |
| | 40 | 95 | 95 |

| | |
|---|---|
| Solvent | 60% acetonitrile |
| Sample processing method: | 2 mg of sample is dissolved into 10 ml solvent, and prepared in situ. |

TABLE F

Stability of the compounds at 25° C. for one month.

| Compound | Day 0 (purity) | Day 30 at 0° C. (purity) | Day 30 at 25° C. (purity) |
|---|---|---|---|
| 2 | 97.28% | 92.58% | 86.14% |
| 3 | 99.24% | 99.18% | 99.16% |
| 4 | 97.23% | 97.13% | 97.25% |
| 5 | 99.05% | 99.01% | 99.05% |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed. It is intended that the following claims define the scope of the disclosure and that methods and structures within the scope of these claims and their equivalents be covered thereby.

The invention claimed is:

1. A compound according to Formula I:

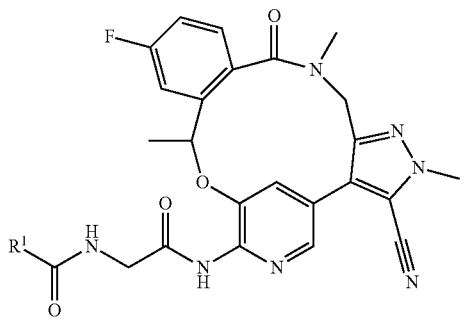

I or a pharmaceutically acceptable salt, solvate, or enantiomer thereof, wherein
R$^1$ is C$_{1-6}$ alkyl, or C$_{1-6}$ alkoxy, provided that R$^1$ is not tert-butoxyl.

2. The compound of claim 1, wherein the compound is accordingly to Formula II:

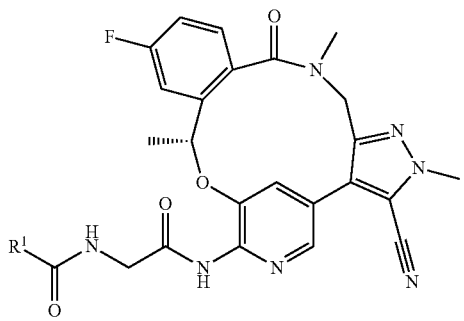

II or a pharmaceutically acceptable salt, solvate, or enantiomer thereof, wherein
R$^1$ is C$_{1-6}$ alkyl, or C$_{1-6}$ alkoxy.

3. The compound of claim 2, or the pharmaceutically acceptable salt, solvate, or enantiomer thereof, wherein R$^1$ is methyl, ethyl, n-propyl, isopropyl, n-butyl, sec-butyl, isobutyl, or tert-butyl.

4. The compound of claim 3, or the pharmaceutically acceptable salt, solvate, or enantiomer thereof, wherein R$^1$ is methyl.

5. The compound of claim 2, or the pharmaceutically acceptable salt, solvate, or enantiomer thereof, wherein R$^1$ is methoxyl, ethoxyl, n-propoxyl, isopropoxyl, n-butoxyl, sec-butoxyl, or iso-butoxyl.

6. The compound of claim 5, or the pharmaceutically acceptable salt, solvate, or enantiomer thereof, wherein R$^1$ is methoxyl.

7. The compound of claim 5, or the pharmaceutically acceptable salt, solvate, or enantiomer thereof, wherein R$^1$ is ethoxyl.

8. The compound of claim 1, or the pharmaceutically acceptable salt, solvate, or enantiomer thereof, wherein the compound is selected from the group consisting of:

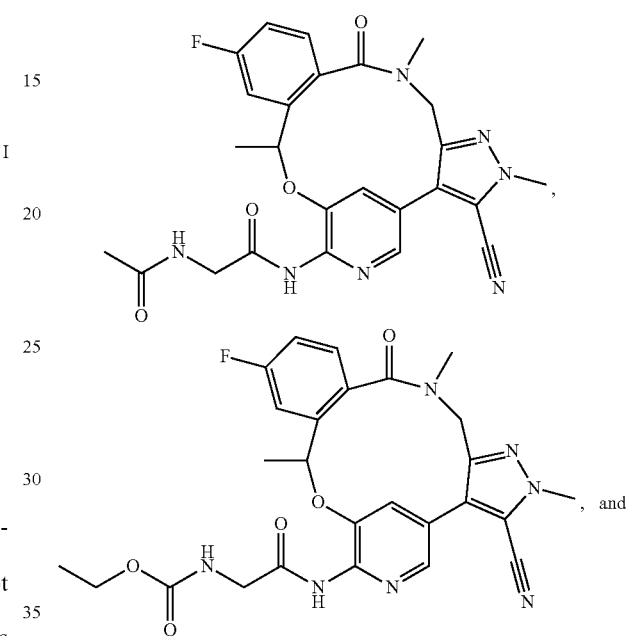

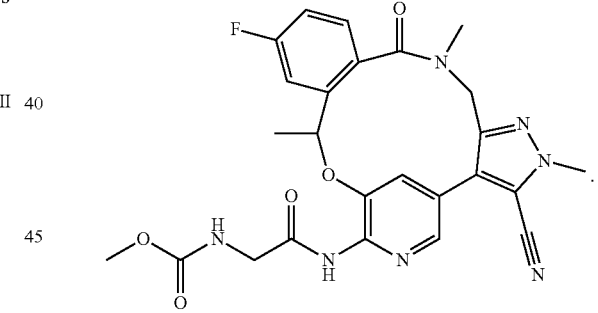

9. The compound of claim 2, or the pharmaceutically acceptable salt, solvate, or enantiomer thereof, wherein the compound is selected from the group consisting of:

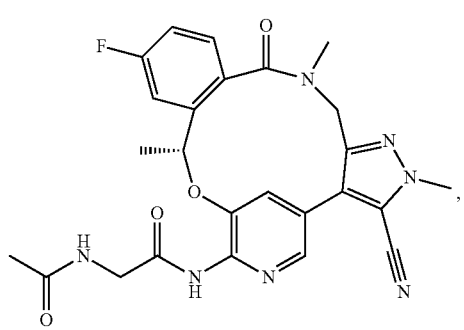

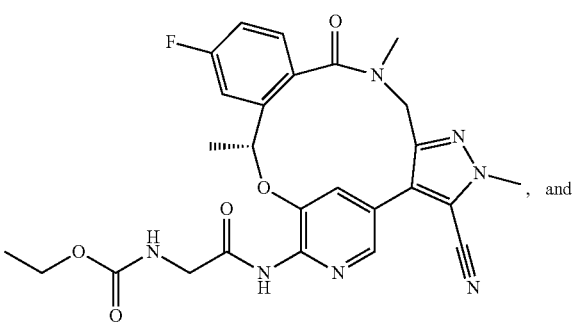

, and

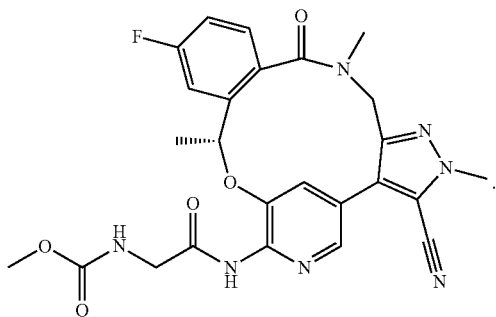

.

10. A pharmaceutical composition comprising a compound of claim 1 and a pharmaceutically acceptable carrier.

11. The pharmaceutical composition of claim 10, further comprising one or more anti-cancer agents for treating neoplasia.

12. The pharmaceutical composition of claim 10, wherein the compound is selected from the group consisting of:

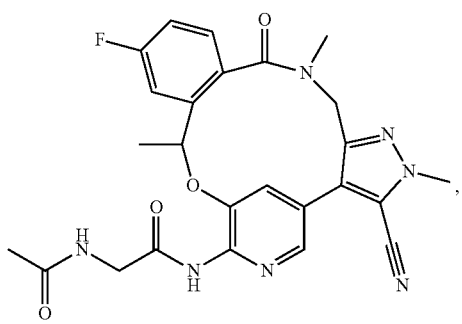

,

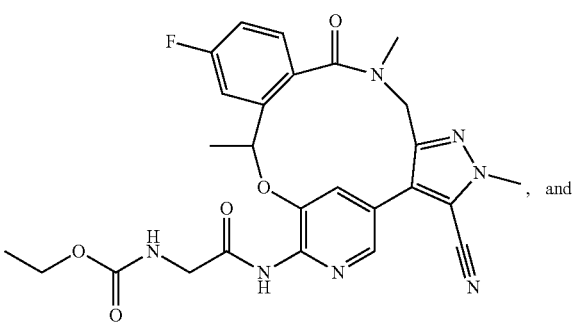

, and

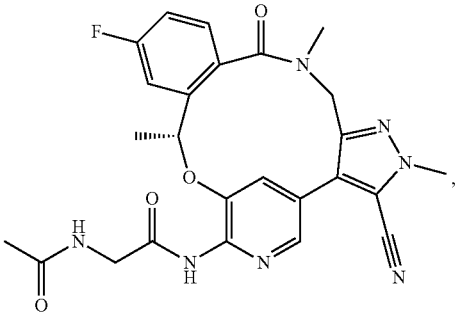

.

13. A pharmaceutical composition comprising a compound of claim 2 and a pharmaceutically acceptable carrier.

14. The pharmaceutical composition of claim 12, further comprising one or more anti-cancer agents for treating neoplasia.

15. The pharmaceutical composition of claim 13, wherein the compound is selected from the group consisting of:

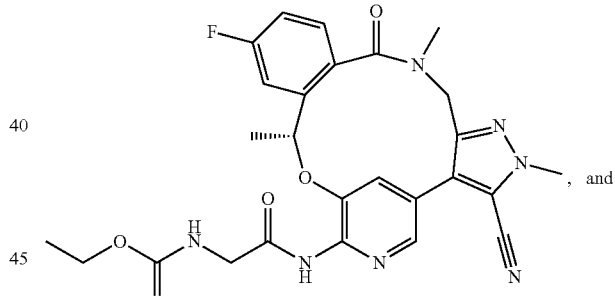

,

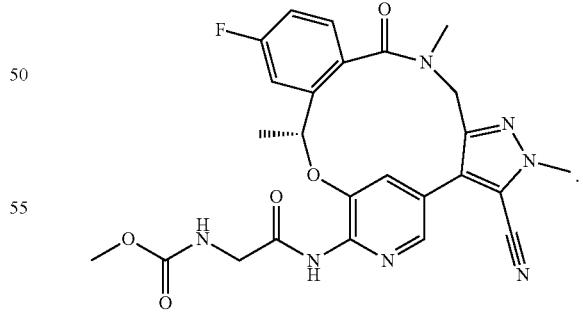

, and

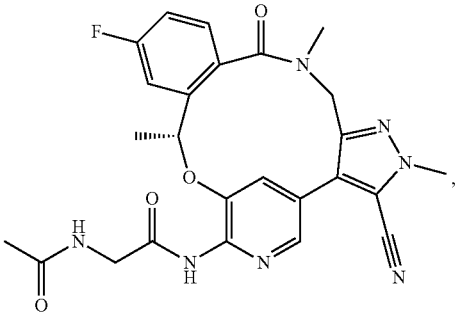

.

16. A method of treating a disease in an individual, comprising: administering to the individual a therapeutically effective amount of a pharmaceutical composition comprising a compound of claim 1, wherein the disease is lung cancer, brain cancer, neoplasia, a hyper-proliferative disorder, or ALK, ROS1, and/or NTRK kinases mediated disorder.

17. The method of claim 16, wherein the compound is selected from the group consisting of:
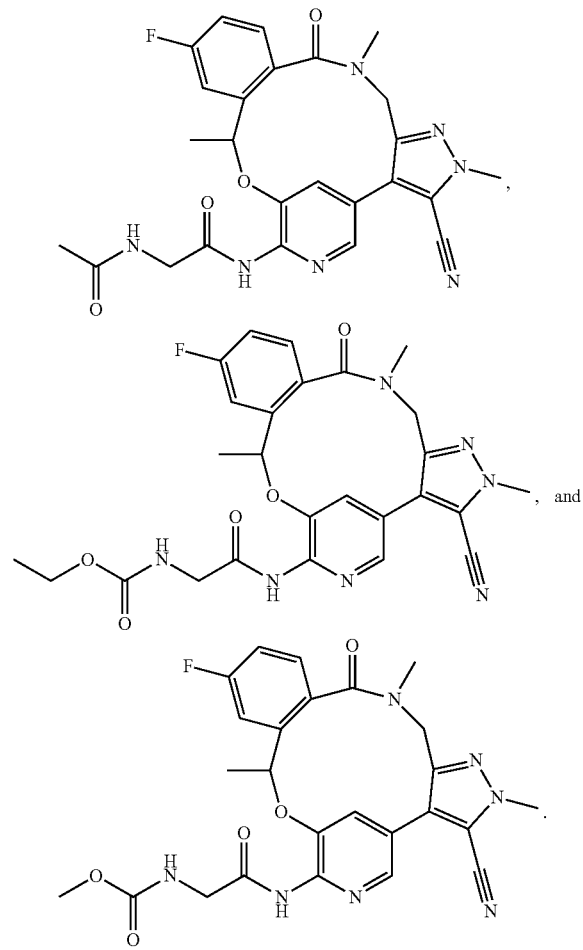
18. The method of claim 16, wherein the compound is selected from the group consisting of:
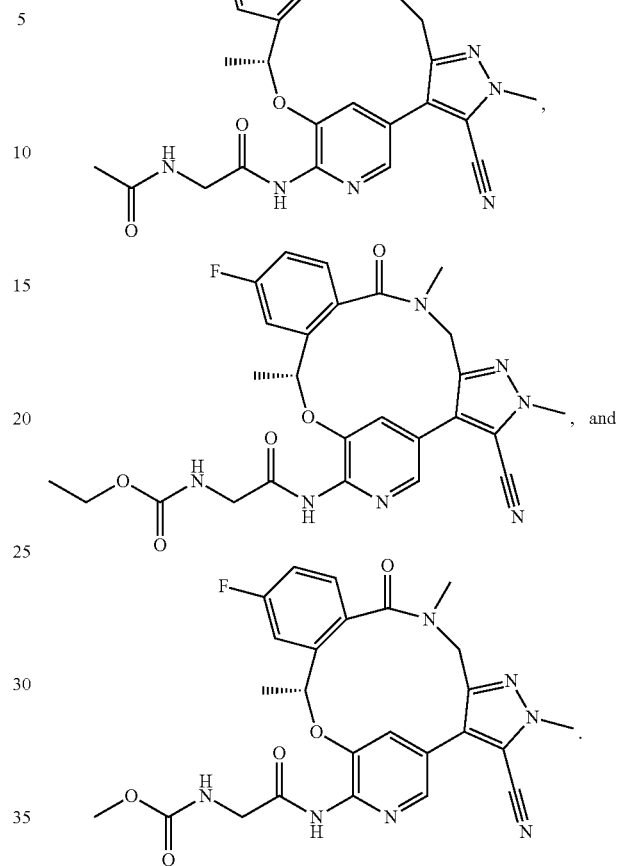
19. The method of claim 16, wherein the disease is lung cancer, brain cancer, or neoplasia.
20. The method of claim 16, wherein the disease is ALK, ROS1, and/or NTRK kinases mediated disorder.
* * * * *